United States Patent [19]

Imamura et al.

[11] Patent Number: 5,126,246
[45] Date of Patent: Jun. 30, 1992

[54] REAGENT FOR ANALYSIS OF TRIGLYCERIDES AND ANALYSIS USING THE SAME

[75] Inventors: Shigeyuki Imamura; Mamoru Takahashi; Hideo Misaki; Kazuo Matsuura, all of Shizuoka, Japan

[73] Assignee: Toyo Jozo Company, Ltd., Shizuoka, Japan

[21] Appl. No.: 435,003

[22] Filed: Nov. 9, 1989

Related U.S. Application Data

[63] Continuation-in-part of Ser. No. 328,457, Mar. 24, 1989, abandoned.

[30] Foreign Application Priority Data

Apr. 15, 1988 [JP] Japan .................................. 63-92912

[51] Int. Cl.⁵ .............................................. C12Q 1/44
[52] U.S. Cl. ........................................ 435/19; 435/11;
435/15; 435/18; 435/20; 435/25; 435/28;
435/198; 435/810; 435/832; 436/63; 436/71;
436/815; 530/825; 530/830
[58] Field of Search ........................ 435/15, 18, 19, 25,
435/28, 810, 832, 11, 20, 198; 436/63, 71, 815;
530/825, 830

[56] References Cited

U.S. PATENT DOCUMENTS

| 4,056,442 | 11/1977 | Huang et al. ........................ 195/62 |
| 4,999,289 | 3/1991 | Akiba et al. ........................ 435/19 |

FOREIGN PATENT DOCUMENTS

| 19253 | 11/1980 | European Pat. Off. . |
| 101046 | 2/1984 | European Pat. Off. . |
| 285101 | 10/1988 | European Pat. Off. . |
| 41-7836 | 4/1966 | Japan . |
| 55-42532 | 3/1980 | Japan . |
| 56-28516 | 7/1981 | Japan . |
| 56-28517 | 7/1981 | Japan . |
| 57-8797 | 2/1982 | Japan . |
| 57-42312 | 9/1982 | Japan . |
| 57-52835 | 11/1982 | Japan . |
| 57-59753 | 12/1982 | Japan . |
| 62-80299 | 10/1988 | Japan . |

OTHER PUBLICATIONS

Research Disclosure, vol. 275, Mar. 1987.
Fredrickson et al., Biochem. Biophys. Acta 876:288-293(1986).
Pope et al., J. Biol. Chem. 241:2306-2310(1966).
Kosugi et al., J. Ferment. Technol.. 49:968, 1971.
Weaber et al., Appl. Micro. 21:639, 1971.
Troller et al., Appl. Micro. 20:480, 1970.
Oterholm et al., Appl. Micro 20:16, 1970.
Kokusho et al., Agric. Biol. Chem. 46:1159, 1982.

Primary Examiner—Margaret Moskowitz
Assistant Examiner—Ardin Marschel
Attorney, Agent, or Firm—Darby & Darby

[57] ABSTRACT

Reagent for analysis of triglycerides contained in blood serum is provided, which comprises lipases and monoglyceride lipases capable of acting on monoglycerides having substrate specificity and capable of catalyzing the following enzymatic reaction: monoglyceride + $H_2O$ → glycerol + fatty acids. The glycerol or fatty acids are measured to learn an amount of the triglycerides or fatty acid by any known analytical method.

13 Claims, 5 Drawing Sheets

OPTIMUM pH

REAGENT FOR ANALYSIS OF TRIGLYCERIDES AND ANALYSIS USING THE SAME

This is a continuation-in-part application of Ser. No 07/328,437 filed March 24, 1989 now abandoned.

BACKGROUND OF THE INVENTION

The present invention relates to a reagent useful for analysis of triglyceride and an analysis method of triglyceride and an analysis method using the same.

More specifically, the present invention relates to a reagent comprising lipases and monoglyceride lipases, which is useful for the rapid quantitative analysis of triglyceride, particularly those contained in blood serum, and an improved method for the analysis of triglycerides using the same.

The triglyceride contained in samples, particularly those such as body fluids, has been analyzed in such a manner that the triglyceride is hydrolyzed usually using lipases ultimately up to glycerol and fatty acid through diglyceride and successive monoglyceride, and then the glycerol or fatty acid liberated from the triglyceride is assayed by a method taking advantage of an enzymatic or chemical reaction. The assay is conducted, for example, in a simple manner, by the use of electrodes or indicators.

In order to perform an effective analysis of triglyceride contained in blood serum, proteolytic enzymes such as proteases and lipoprotein lipases have been used for liberation of triglyceride from bound proteins, followed by analyzing the triglyceride. Japanese Patent Publication No. 9518/1979 (Japanese Patent Application No. 114493/1978) proposes to use both lipases and proteases. In addition, in order to promote the hydrolysis reaction of triglycerides to form glycerol, a combination of various lipases having different properties from each other, and an addition of surface active agents or chemical agents to the sample solution have been proposed. There are, for example, hydrolysis using a combination of lipases having different properties from each other (Japanese Patent Laid-Open No. 25694/1977, Japanese Patent Publication No. 29/1981 and Japanese Patent Publication No. 28276/1982), hydrolysis using a combination of lipases and cholesterol esterases (Japanese Patent Publication No. 46799/1981), hydrolysis using a combination of lipases and surface active agents (Japanese Patent Publication No. 39158/1982), hydrolysis using a combination of lipases, surface active agents, and phenol or aniline derivaties (Japanese Patent Publication No. 5677/1983), hydrolysis using a combination of lipases, carboxyesterase originated from pig livers and alkali metal or alkaline earth metal alkylsulfates (Japanese Patent Laid-Open No. 64495/1974), and hydrolysis using lipases, pancreatic lipases and salts of bile acid (Japanese Patent Laid-Open No. 11987/1977).

As described above, the conventional analytical methods have been carried out by separating triglyceride from bound proteins, and promoting the hydrolysis reaction of triglyceride to produce glycerol. However, the hydrolysis rate is not so speedy that a considerable period of time is needed for the analysis, since almost all lipases used in these methods are capable of hydrolyzing the triglyceride up to glycerol, but they are not active enough on the β-monoglyceride produced by the hydrolysis of triglyceride, i.e., have low activity in hydrolyzing monoglyceride to glycerol. Therefore, it has been desired to accelerate the hydrolysis reaction of the monoglyceride to produce glycerol and shorten the period of time for analysis.

The present inventors succeeded in isolating a monoglyceride lipase-producing microorganism belonging to *Bacillus stearothermophilus* H-165 strain, which is able to catalyze the hydrolysis reaction from monoglyceride to glycerol, from the soil around the hot spring of the spa of Kirishima, Kagoshima-ken, Japan, and a monoglyceride lipase is obtained by the cultivation thereof (Japanese Patent Application No. 80299/1987). The inventors have also found that the resulting monoglyceride lipase is capable of acting on α- or β-monoglyceride extremely strongly unlike the conventional lipases which act weakly on the monoglyceride. Moreover, it has been found that the monoglyceride lipase has an optimum pH value of around 5, an isoelectric point of 4.6 and a molecular weight of as low as 27,000, shows a maximum activity at an optimum temperature of 75° C., and is excellent in the heat resistance so that it is hardly inactivated at 70° C. and holds the activity by 20 % even after the treatment at 90° C.

The present inventors have further studied extensively to find that the combined use of the monoglyceride lipase and lipases is able to shorten the period of time required for the analysis of the triglyceride contained in a sample solution, because the monoglyceride lipase specifically strongly acts on the monoglyceride formed from the triglyceride through diglyceride by the action of lipase, resulting in the acceleration of the hydrolysis reaction from the triglyceride to glycerol.

SUMMARY OF THE INVENTION

The present invention accomplished on the basis of the above-said findings provides a reagent for the analysis of triglyceride, which comprises lipases and monoglyceride lipases. Furthermore, it provides a reagent for the analysis of triglyceride, which comprises lipases, monoglyceride lipases and reagents for assaying glycerol. The present invention also provides a method for the analysis of triglyceride by bringing lipases into contact with a sample solution containing triglyceride, and assaying liberated glycerol or fatty acid, which comprises a system containing the monoglyceride lipase to react with the sample solution, and then assaying components consumed or produced in the reaction for assaying the glycerol or fatty acids.

The above and other objects, features and advantages of the present invention will be apparent from the following description and the appended claims, taken in conjunction with the accompanying drawings, in which:

DETAILED DESCRIPTION OF THE PREFERRED EMBODIMENT

The monoglyceride lipase usable in the present invention is not particularly limited, as far as it is capable of strongly catalyzing at least the reaction where glycerol and fatty acid are produced from $\beta$-monoglyceride, and incapable or hardly capable of acting on triglyceride and diglyceride. A preferred one is produced by culturing Bacillus stearothermophilus H-165 (FERM BP-1673) in a culture medium. In the present invention, any strains may be used as long as they are capable of producing the monoglyceride lipase which acts strongly on the monoglyceride. The present invention will be illustrated in more detail with reference to the monoglyceride lipase obtained using Bacillus stearothermophilus H-165 strain (FERM BP-1673) as follows.

(1) Performance:

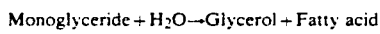

Monoglyceride + H$_2$O → Glycerol + Fatty acid (Monoglyceride may be either $\alpha$-monoglyceride or $\beta$-monoglyceride.)

(2) Molecular weight: 27,000±2,700 [Measured using a column of a polyvinyl gel "TSK3000SW" (trade name; product of Toyo Soda Mfg., Co., Ltd.) and a 50 mM phosphate buffer (pH 6.5) containing 0.2 M of NaCl as a mobile phase.]

Figure 2:
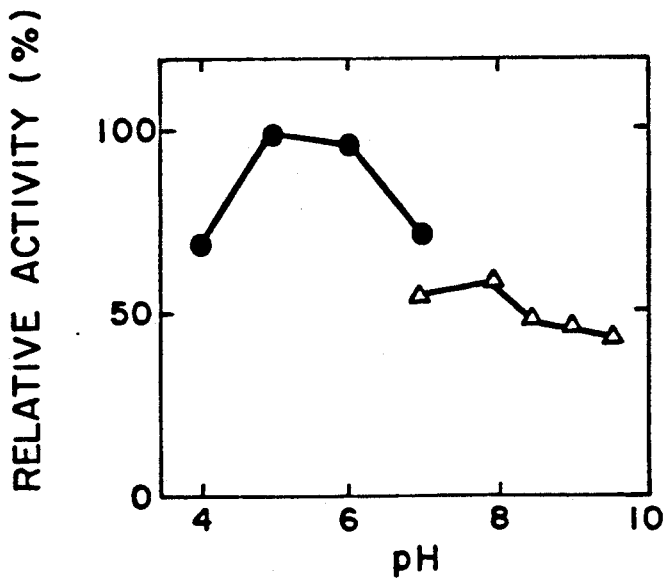
FIG. 2 shows an optimum pH curve of the monoglyceride lipase used in this invention.

(3) Optimum pH: A measurement method of enzymatic activity to be described subsequently is employed. Monolaurin and the enzyme are allowed to react with each other for 10 minutes by separately using a dimethylglutarate buffer(pH 4–7; –●– in FIG. 2) and a tris-HCl buffer (pH 7–9.5; –△– in FIG. 2) as buffers. The reaction mixture is thereafter boiled for 2 minutes to inactivate the enzyme, thereby terminating the reaction. The reaction mixture is then incubated at 37° C., followed by enzymatic measurement of the amount of glycerin formed. Results are shown in FIG. 2. The optimum pH is around pH 5.

Figure 3:
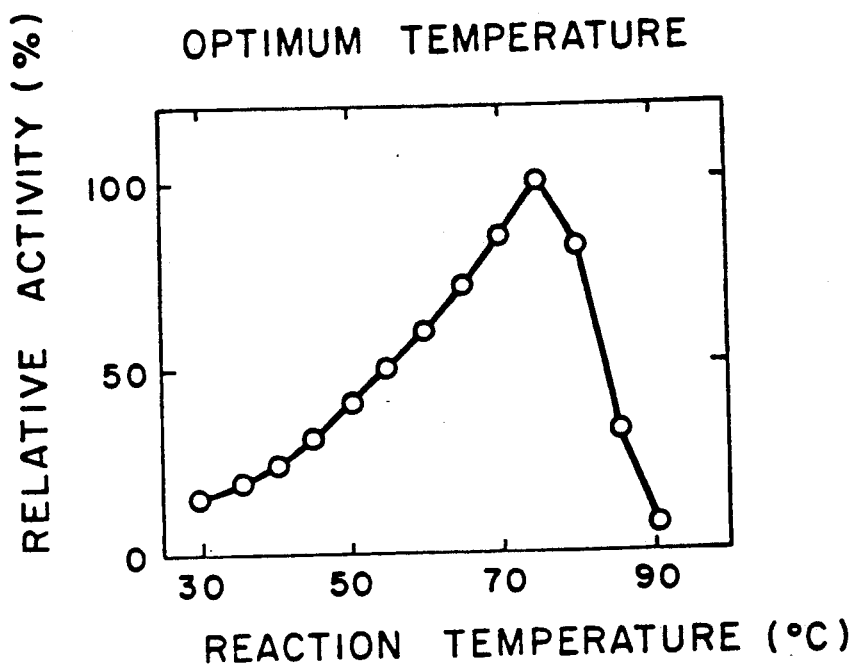
FIG. 3 shows an optimum temperature curve of the same enzyme as that in FIG. 2.

(4) Optimum temperature: Using a PIPES-NaOH buffer (pH 7.3), reactions are carried out separately at individual temperatures shown in FIG. 3. The reaction mixtures are separately boiled subsequent to their corresponding reactions. Following the below-described measurement method, the amounts of glycerin formed are separately measured. Results are shown in FIG. 3. The maximum activity is exhibited at 75° C.

Figure 4:
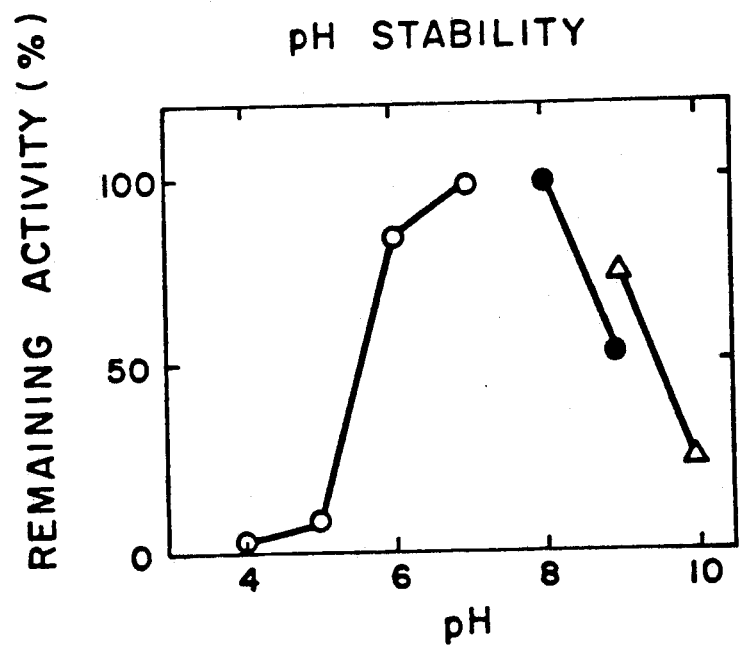
FIG. 4 shows a pH stability curve of the same enzyme as that in FIG. 2.

(5) pH stability: Solutions (1.0 U/ml) of the present enzyme are separately prepared with 10 mM dimethylglutaric acid-NaOH buffer (pH 4–7; –O– in FIG. 4), tris-HCl buffer (pH 8–9, –●– in FIG. 4) and glycine NaOH buffer (pH 9–10; –△– in FIG. 3). After the individual solutions are incubated at 75° C. for 10 minutes, its residual activity is measured in accordance with the below-described assay method of enzymatic activity. Results are shown in FIG. 4. The enzymatic activity remains stable in a pH range of 7–8.

Figure 5:
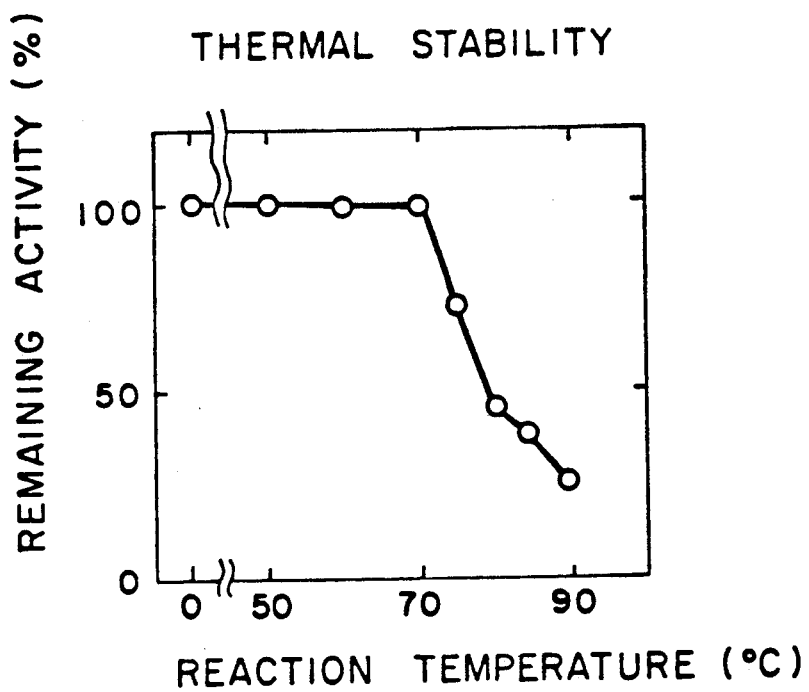
FIG. 5 shows a thermal stability curve of the same enzyme as that in FIG. 2.
Figure 6:
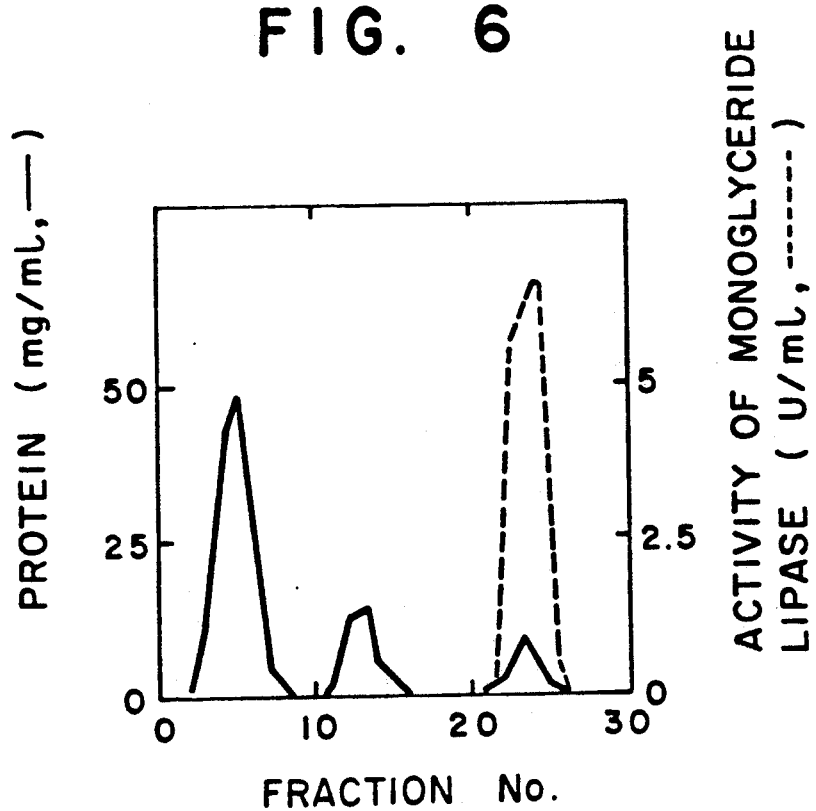
FIG. 6 shows an elution curve in the purification process for the same enzyme as that in FIG. 2.
Figure 7:
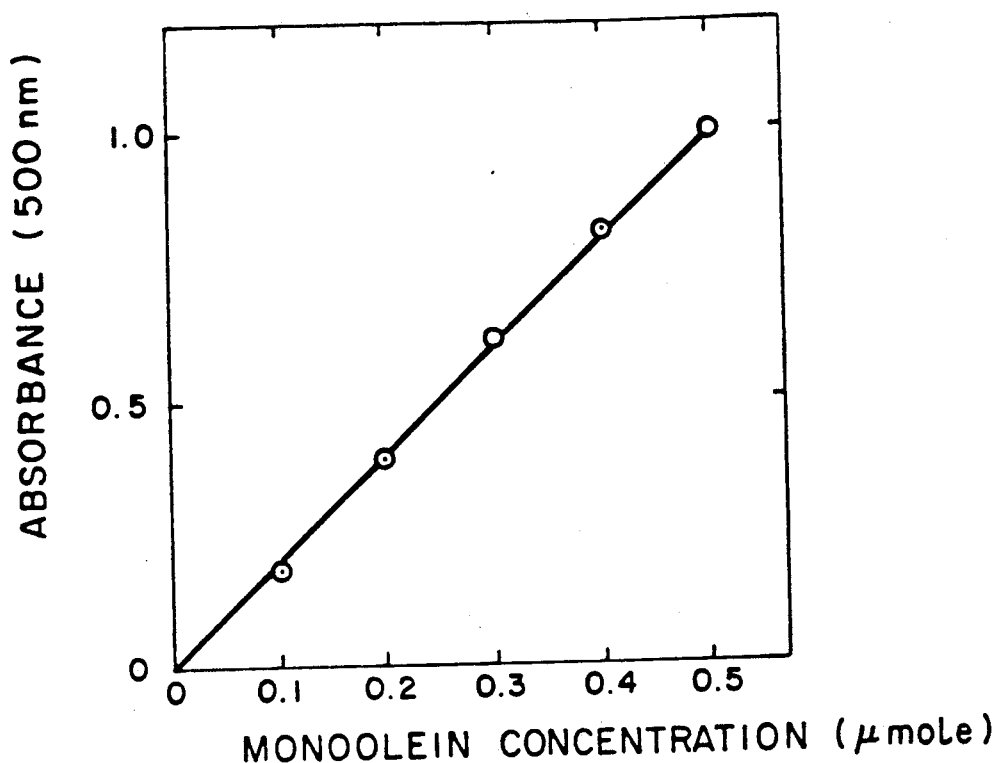
FIG. 7 shows a calibration curve of the monoglyceride.

(6) Thermal stability: A solution (1.0 U/ml) of the present enzyme is prepared with 10 mM tris-HCl buffer (pH 7.5). After the solution is incubated for 10 minutes at individual temperatures shown in FIG. 5, the residual activity is measured in accordance with the below-described assay method of enzymatic activity. Results are shown in FIG. 5. The enzymatic activity remains stable up to 70° C.

(7) Isoelectric point: pH 4.6±0.4 (After a current of a constant voltage of 700 V is applied to at 4° C. for 40 hours by isoelectric focusing electrophoresis making use of an ampholyte as a carrier, the enzymatic activity of each fraction is measured.

(8) Substrate specificity: The substrate specificity of the monoglyceride lipase in this invention is investigated under conditions where the below-described assay method of enzymatic activity for the monoglyceride lipase is conducted. As a result, as summarized in Table 1, the maximum activity is exhibited against $\alpha$-monolaurin. The monoglyceride lipase does not act on diglyceride or triglyceride as substrates, since no glycerol hydrolyzed is detected from those substrates in the presence of the monoglyceride lipase, when diglyceride derived from yolk lecithin, 1,2-dilinolein, 1,3-dilinolein and triolein are used as substrate.

An action of the monoglyceride lipase on $\beta$-monoglyceride as a substrate specificity is as follows.

(1) Confirmation of a fatty acid liberated from $\alpha$-linoleoyl-$\beta$-oleoyl-diglyceride as a substrate, by high performance liquid chromatography (HPLC):

(i) Pancreatic lipase (50 μl) is added to 1.0 ml of a reaction mixture having a composition of 0.5 mg of $\alpha$-linoleoyl-$\beta$-oleoyl-diglyceride, 1.8 mg of a nonionic surface active agent ("Triton X-100", trade name; a product of Sigma Chemical Company), 3.8 mg of deoxycholic acid, 20 U of colipase, 0.15 mg of calcium chloride, and 200 μl of 0.1M N-tri(hydroxymethyl) methyl-3-aminopropanesulfonic acid (TAPS)-NaOH (pH 8.3). After the mixture is allowed to react at 37° C. for 10 minutes, the reaction is terminated. A 15 μl aliquot of the reaction mixture is applied to a column and subjected to high performance liquid chromatography under the following conditions.

Column: "Zorbox ODS" (trade name; 4.6 mm$\phi$×25 cm)

Solvent: acetonitrile: H$_2$O (96:4)

Detection: ultraviolet absorption at 205 nm

Flow rate: 1.2 ml/min

As a result, no oleic acid but linoleic acid is detected at the retention time of 23 minutes. This detection of the linoleic acid bound at the $\alpha$-position shows that pancreatic lipase acts only on the $\alpha$-position of an $\alpha,\beta$-diglyceride substrate to hydrolyze until $\beta$-oleoyl-monoglyceride is produced.

(ii) The monoglyceride lipase (0.5 U) is added to a reaction solution of the same composition as that employed above and a reaction is allowed to proceed in the similar manner to the above. Fatty acids liberated are detected by high performance liquid chromatography, i.e., linoleic acid and oleic acid are confirmed at the retention times of 23 minutes and 31 minutes, respectively. This result shows that the monoglyceride lipase acts on $\beta$-monoglyceride substrate produced from $\alpha,\beta$-diglyceride by pancreatic lipase until linoleic acid bound at the $\beta$-position is liberated. Glycerol liberated from the $\alpha,\beta$-diglyceride is also detected.

(2) Substrate specificity of the monoglyceride lipase upon use of $\alpha,\beta$-diglyceride as a substrate:

(i) Pancreatic lipase and the monoglyceride lipase are applied to the below-described $\alpha,\beta$-diglyceride substrates. Their α-positions are hydrolyzed by the pancreatic lipase and then the resulting β-monoglycerides are allowed to react with the monoglyceride lipase, in order to analyze glycerol thus liberated. Glycerol is detected with respect to the substrates, namely,α-oleyl-β-palmitoyldiglyceride, α-palmitoly-β-oleolyldiglyceride and α,β-dilinoleylglyceride. However, glycerol is not detected when only pancreatic lipase is used.

(9) Effects of surface active agent and metal ions: When surface active agent such as "Triton X-100" (trade name) and cholic acid are added, it is clear from Table 2 that inhibition of the activity is observed in the high concentration range. The monoglyceride lipase is not affected by the addition of divalent metal ions such as $Ca^{++}$ and $Mg^{++}$.

TABLE 1

Substrate Specificity of the Monoglyceride Lipase

| Substrate | Activity of lipase (%) |
|---|---|
| α-monoglyceride: | |
| Monoacetin | 10.1 |
| Monobutyrin | 47.1 |
| Monocaprin | 89.1 |
| Monolaurin | 100.0 |
| Monomyristin | 85.7 |
| Monopalmitin | 39.5 |
| Monostearin | 27.6 |
| Monoolein | 56.3 |
| β-monoglyceride: | |
| Monoolein | 75.6 |
| Diglycerides: | |
| Derived from yolk lecithin* | 0 |
| 1,2-dilinolein | 0 |
| 1,3-dilinolein | 0 |
| Triglyceride: | |
| Triacetin | 0 |
| Tributyrin | 0 |
| Triolein | 0 |

*Preparation method: Phospholipase C is allowed to react purified yolk lecithin. A fraction extracted by chloroform-methanol is used.

TABLE 2

Effects of Surface Active Agents and Metal Ions on the Monoglyceride Lipase

| Reagent | Concentration | Activity of lipase (%) |
|---|---|---|
| — | — | 100 |
| Triton X-100 | 0.1% | 81.7 |
| Triton X-100 | 0.5% | 46.5 |
| Cholic acid | 1 mM | 100.0 |
| Cholic acid | 10 mM | 92.6 |
| $CaCl_2$ | 1 mM | 100.0 |
| $MgCl_2$ | 1 mM | 100.0 |
| EDTA | 1 mM | 86.0 |

MEASUREMENT METHOD OF ENZYMATIC ACTIVITY OF MONOGLYCERIDE LIPASE

| | |
|---|---|
| 0.2M PIPES-NaOH buffer (pH 7.3) | 0.1 ml |
| 0.3% 4-Aminoantipyrine | 0.05 ml |
| 0.2% TOOS** | 0.05 ml |
| (45 U/ml) Peroxidase | 0.05 ml |
| 20 mM $MgCl_2$ | 0.025 ml |
| 20 mM ATP | 0.025 ml |
| (25 U/ml) Glycerol kinase | 0.01 ml |
| (1000 U/ml) Glycerophosphate oxidase | 0.015 ml |
| Purified water | 0.075 ml |

**TOOS: N-ethyl-N-(2-hydroxy-3-sulfopropyl)-meta-toluidine)

To 0.4 ml of a solution of the above composition, is added 50 μl of 10 mM monolaurin (0.5 % aqueous solution of "Triton X-100"). The resultant mixture is pre-incubated at 37° C. for 2–3 minutes and 50 μl of an enzyme solution is added to initiate a reaction. Exactly 10 minutes later, 2.5 ml of 5 % SDS (sodium dodecyl sulfate) is added to terminate the reaction. The absorbance is measured at 550 nm. Regarding the enzymatic activity, the activity capable of producing 1 μmole of glycerol per minute is defined at 1 Unit (1 U). The following equation is used for calculation of enzymatic activity (potency):

$$\text{Enzymatic activity (U/ml)} = \Delta A\,550 \times \frac{2.95}{18.0} \times \frac{1,000}{50} \times \frac{1}{10}$$

wherein
ΔA 550: Absorbance at the wavelength of 550 nm
2.95: Total volume of reaction mixture (ml)
18.0: Millimolar extinction coefficient of hydrogen peroxide ($cm^2/\mu mole$)
50: Volume of enzyme solution used (μl)
10: Reaction time (min)

The above description demonstrates that the enzyme obtained by the incubation of *Bacillus stearothermophilus* H-165 strain (FERM BP-1673) has the substrate specificity on the monoglyceride, and is able to catalyze the reaction;

monoglycerides + $H_2O \rightarrow$ glycerol + fatty acids.

*Bacillus stearothermophilus* H-165 strain, one example of microorganisms capable of producing the monoglyceride lipase, has the following taxonomical properties.

A. Visual observation:
Cultured at 50°–55° C. for 18–44 hours.
(1) Nutrient agar slant culture:
Presents a gray white color tinged in a yellow color. Grows in the filiform. The growth is good and no soluble pigment is produced.
(2) Nutrient agar flat culture:
Shows a gray color tinged in a yellow color. A circular flat entire colony is formed but no soluble pigment is produced.
(3) Liquid medium:
Good growth is observed. The medium becomes turbid uniformly.
(4) BCP milk medium:
The medium remains unchanged.

B. Morphological characteristics:
(1) Shape and arrangement:
The strain is a cylindrical bacillus which is either straight or is slightly bent at one or both ends. Cells are either discrete or bound together two by two. Short chains may be formed occasionally.
(2) Size:
0.6–0.8×2.5–4.0 μm.
(3) Mobility:
None.
(4) Spore:
A spore in the shape of an egg or an elongated circle is found at a central part of each cell or at a location close to the contour of each cell. Its size is 0.8–1.2×1.5–2.0 μm. The cell expands by the spore.
(5) Polymorphism:
None.

C. Physiological and biochemical characteristics:

| | |
|---|---|
| Gram stain | + |
| KOH Reaction | − |
| Acid-fast stain | − |
| Capsule formation | − |
| OF test (Hugh-Leifson medium) | No changes |
| OF test (modified medium)*** | 0 (oxidized) |
| Growth under anaerobic conditions | − |
| Growth temperature 60° C. | + |
| 50° C. | + |
| 47° C. | + |
| Growth pH 8.6 | − |
| 7.7 | + |
| 5.6 | + |
| 4.4 | − |
| Salt resistance 0% | + |
| 3% | + |
| 5% | − |
| Hydrolysis of gelatin | − |
| Hydrolysis of starch | + |
| Hydrolysis of casein | − |
| Hydrolysis of aesculin | + |
| Hydrolisis of cellulose | − |
| Hydrolysis of arginin | + |
| Production of catalase | + |
| Production of oxidase | + |
| Production of urease (SSR medium) | − |
| Production of urease (Chris. medium) | + |
| Production of indole | − |
| Production of hydrogen sulfide | − |
| Production of acetoin | − |
| MR test | − |
| Reduction of nitrates | + |
| Denitrification | − |
| *** Medium composition: | |
| (NH₄)₂HPO₄ | 1.0 g |
| MgSO₄.7H₂O | 0.2 g |
| Glucose | 10.0 g |
| BTB (0.2% aq. soln.) | 10.0 g |
| KCl | 0.2 g |
| Yeast extract | 1.0 g |
| Agar | 3.0 g |
| Distilled water | 1000.0 ml |
| (ph 7.0) | |
| Assimilation test (Simons medium): | |
| Citric acid salts | − |
| Maleic acid salts | − |
| Malic acid salts | + |
| Gluconic acid salts | + |
| Propionic acid salts | − |
| Malonic acid salts | − |
| Succinic acid salts | + |
| Assimilation test (Christensen medium): | |
| Citric acid salts | + |
| Maleic acid salts | − |
| Malic acid salts | + |
| Gluconic acid salts | + |
| Propionic acid salts | + |
| Malonic acid salts | − |
| Succinic acid salts | + |
| Production of gas from glucose | − |
| Production of acids from sugars [(NH₄)₂HPO₄ is used as an N source] | |
| Adonitol | − |
| L(+)-Arabinose | − |
| Cellobiose | + |
| Dulcitol | − |
| Meso-erythritol | − |
| Fructose | + |
| Galactose | − |
| Glucose | + |
| Glycerin | + |
| Inositol | − |
| Inulin | − |
| Lactose | − |
| Maltose | + |
| Mannitol | + |
| Mannose | + |
| Melezitose | + |
| Melibiose | + |
| Raffinose | + |
| L(+)-Rhamnose | − |

-continued

| | |
|---|---|
| D-Ribose | + |
| Salicin | + |
| Sorbitol | − |
| Sorbose | − |
| Starch | + |
| Sucrose | + |
| Trehalose | + |
| Xylose | + |

From the taxonomical properties described above, the strain H-165 may be defined as a thermophilic temperature aerobic bacterium which is a non motile cylindrical bacillus having a straight shape or slightly bent end or ends, is gram-positive, has a size of 0.6−0.8×2.5−4.0 μm, forms a spore and undergoes cell expansion by the spore, decomposes glucose oxidatively and produces an acid, and is positive for catalase and oxidase productivity. The strain having such various characteristics is judged to fall witin the family of Bacillus, because it is a spore-forming, gram-positive, aerobic and rod-shaped bacterium. As other mciroorganism strains showing the same characteristics as the above strain with respect to acetoin productivity, indole productivity, gas productivity from gloucose and growing ability under anaerobic conditions, there are (A) *Bacillus sterothermophilus*, (B) *Bacillus alcalophilus*, (C) *Bacillus badius* and (D) *Bacillus firmus*. The taxonomical properties of these bacterium species and those of the strain H-165 are compared as follows: [+: positive, −: negative, d: different depending on strains, ND: no available data ].

| | A | B | C | D | Strain H-165 |
|---|---|---|---|---|---|
| Gram stain | + | + | + | + | + |
| Cell expansion by spore | d | − | − | − | + |
| Anaerobic growth | − | − | − | − | − |
| Catalase production | + | + | + | + | + |
| Gelatin hydrolysis | + | + | ND | + | − |
| Starch hydrolysis | + | + | − | + | + |
| Casein hydrolysis | d | + | + | + | − |
| Indole production | − | − | − | − | − |
| Acetoin production | − | − | − | − | − |
| Reduction of nitrates | d | − | − | d | + |
| Assimilation of citric acid salts | d | − | − | − | − |
| Production of gas from glucose | − | − | − | − | − |
| Production of acid from L-arabinose | d | + | − | − | − |
| Production of acid from D-glucose | + | + | − | + | + |
| Production of acid from mannitol | d | + | − | + | − |
| Production of acid from D-xylose | d | + | − | − | + |
| Growth at 60° C. | + | − | − | − | + |

From the above comparison, the characteristics of the strain H-165 are found to conform very well to those of *Bacillus sterothermophilus* except for gelatin degradability. Therefore, the strain H-165 is identified as a strain belonging to *Bacillus sterothermophilus*, named *Bacillus sterothermophilus* H-165, and deposited under FERM BP-1673 with Fermentation Research Institute, Agency of Industrial Science and Technology, Ministry of International Trade and Industry, the Government of Japan.

The above-described *Bacillus sterothermophilus* H-165 is merely one example of monoglyceride lipase-producing microorganisms of Bacillus useful in the practice of this invention. The present invention is not limited to the use of this particular strain and any microorganisms capable of producing such monoglyceride lipase may be used in the present invention.

A microorganism capable of producing the monoglyceride lipase is cultured by a method employed routinely in the production of antibiotics, enzymes and the like. The culture may be conducted in either liquid medium or solid medium. For industrial application, it is desirable to inoculate cells of a monoglyceride lipase producing microorganism in a medium and then to subject the cells to submerged aerated-stirring culture.

As nutrient sources for the medium, various nutrient sources employed usually for the culture of microorganisms may be used. As a carbon source, any carbon compound may be used so long as it is assimilable. It is hence possible to use, for example, carbohydrates such as glucose, sucrose, lactose, galactose, maltose, mannitol, sorbitol, dextrin and starch, various organic acids, vegetable oils such as soybean oil and olive oil, animal oils and fats such as lard and fowl oil, etc. As a nitrogen source, any nitrogen compound may be employed so long as it is assimilable. For example, peptone, powdered yeast extract, meat extract, soybean flour, casein, defatted cotton seed flour or the like may be used. In addition, one or more of various satls such as phosphates, magnesium salts, calcium salts, potassium salts, sodium salts, zinc salts, iron salts, manganese salts and halogen salts, corn steep liquor, various vitamins and the like may also be used as needed.

The culturing temperature may be varied suitably within the temperature range in which a microorganism capable of producing the monoglyceride lipase grows and produces the desired enzyme. The preferable culturing temperature may however be 40°-65° C., especially 45°-50° C. Although the culturing time varies depending on the culturing conditions, it is only necessary to terminate the culturing at a suitable time point by watching the timing at which the enzyme reaches the maximum potency. The preferable culturing time is 10-22 hours.

The monoglyceride lipase is then prepared from the thus-cultured broth of the monoglyceride lipase producing microorganism. Since the enzyme is produced intracellularly, the cells are collected from the cultured broth by such a method as filtration or centrifugation. These cells are then disrupted by choosing and combining various cell-disrupting methods such as mechanical disrupting methods, e.g., ultrasonication, processing by a French press and processing by glass beads, and enzymatic disrupting methods, e.g., lysozyme treatment, whereby a crude solution containing the monoglyceride lipase is obtained. A surface active agent such as "Triton X-100" (trade name) may be added as needed.

The monoglyceride lipase is obtained in the purified form from the crude solution by using a known isolation and purification method for proteins, enzymes and the like. The enzyme may be recovered, for example, by fractional precipitation or salt precipitation. The former method is conducted by adding an organic solvent such as acetone, methanol, ethanol or isopropanol to the crude enzyme solution containing the monoglyceride lipase, while the latter method adding ammonium sulfate, sodium chloride, sodium sulfate or the like to the crude enzyme solution. The resultant precipitate may then be purified by one or more of various chromatographic methods such as molecular sieve chromatography and further by electrophoresis, ultracentrifugation or the like until a single peak is indicated. As these purification methods, it is necessary to choose purification methods which make use of properties of the intended monoglyceride lipase. For example, after the above precipitate is dissolved in water or a buffer and if necessary, the resulting solution is dialyzed through a semipermeable membrane, the solution or dialyzate is subjected to ion-exchange chromatography on an anion-exchange resin such as DEAE-cellulose, DEAE-"Sephacel" (trademark), DEAE-"Sepharose" (trademark), DEAE-"Sephadex A-50" (trade name) or DEAE-"Toyo Pearl" (trade mark) or a gel filtration medium such as "Sephadex G-100" (trade name), "Sephadex G-75" (trade name) or "Sephacryl S-200" (trade name). After being applied to two or more of these methods in combination, the monoglyceride lipase is purified by electrophoresis, ultracentrifugation or the like until a single peak is indicated. A stabilizer such as sugar, for example, mannitol, sucrose or sorbitol, an amino acid such as glutamic acid or glycin, or a peptide or protein such as bovine serum albumin is then added, followed by further processing such as lyophilization to obtain powder of the enzyme in a purified form.

The monoglyceride lipase having the physical and chemical properties as described above is only illustrative. The above detailed description on the monoglyceride lipase with respect to the physical and chemical properties, mycological characteristics, identification and naming for the microorganisms from which the lipase is produced, is as described in the specification of Japanese Patent Application No. 80299/1987.

The lipases to be used together ith the above-described monoglyceride lipase for the preparation of the present reagent for analyzing the triglyceride will be illustrated as follows.

Any lipases may be used in the present invention, as long as they are used for quantitative analysis of triglycerides, and are at least capable of catalyzing the hydrolysis reaction of triglycerides to produce diglycerides and fatty acids and that of the diglycerides to produce monoglycerides and fatty acids. Examples are those produced from microorganisms, such as *Rhizopus delemar* (ATCC 4858, ATCC 9374, ATCC 20134 and ATCC 24864), *Rhizopus arrhizus* (ATCC 10260, ATCC 24563 and ATCC 24865), *Chromobacterium viscosum* (ATCC 12472, ATCC 6918, NRRL B-3673 and FERM P-137), *Aspergillus niger* (ATCC 10864, ATCC 1004 and ATCC 1018), *Aspergillus flavus oryzae* (ATCC 9376, ATCC 11495 and ATCC 12891), *Candida lipolytica* (ATCC 8661, ATCC 20287 and ATCC 20363), *Candida cylindracea* (ATCC 14830), *Mucor miehei* (ATCC 16457 and ATCC 26282) and *Mucor pusillus* (ATCC 16458 and ATCC 16459). Lipases obtained from animal sources such as cattle pancreas may be used. Additionally, lipases produced from other known lipase-producing microorganisms may be used, such as those produced from Pseudomonas [Y. Kosugi, J. Ferment. Technol., Vol. 49, 968-980 (1971)], Corynebacterium [K. Weaber, Appl. Microb., Vol. 21, 639-642 (1971)], Staphilococcus [J. A. Troller, Appl. Microb., Vol. 20, 480-484 (1970)], Propionibacterium [A. Oterholm, Appl. Microb., Vol. 20, 16-22 (1970), Alcaligenes [Y. Kokusho, Agric. Biol. Chem., Vol. 46, No. 5, 1159-1164 (1982)], and the like. There are many publications with respect to the lipase produced from the lipase-producing microorganisms belonging to Pseudomonas, such as, for example, Japanese Patent Publication Nos. 7836/1966, 28516/1981, 28517/1981, 42312/1982, 42313/1982, 52835/1982 and 59753/1982. Moreover, enzymes called cholesterol esterases having the same action as the lipases may be used in place of the above lipases. The lipases usable in the present invention are not limited to those described above, and include other known lipases, as well as those obtainable through a genetic engineering process.

The method for measuring the activity of lipases is as follows.

Composotion of Reaction Mixture

|  | (ml) |
|---|---|
| 0.2M Tris-HCl buffer solution (pH 7.5) | 0.2 |
| 27.5 mM Dilinoleoyl glyceride (15% Triton X-100) | 0.05 |
| 50 mM CaCl$_2$ | 0.01 |
| 200 mM ATP | 0.005 |
| 100 mM CoASH | 0.005 |
| Acyl-CoA.synthetase (50 U/ml) | 0.01 |
| Water | Amount so as to make the whole 0.5 ml |

The solution having the above composition (0.5 ml) placed in a test tube is pre-incubated at 37° C. for 2 to 3 minutes, and thereafter an enzyme solution 50 μl) containing 10 mM PIPES-NaOH buffer (pH 7.3) and 0.1 % bovine serum albumin is added thereto. The mixture is allowed to react at 37° C. for 10 minutes. Successively, 10 mM N-ethylmaleimide (0.5 ml) and a reagent (R-2) having the following composition (0.5 ml) are added to the reaction mixture, and the resulting mixture is allowed to react at 37° C. for 5 minutes. Thereafter, the reaction is discontinued by adding 0.5 % sodium dodecylsulfate (1.5 ml). Then, the reaction mixture is determined colorimetrically at a wave length of 550 nm. An activity liberating linoleic acid in an amount of 1 μmole per minutes is regarded to be one unit (1 U).

Composition of the Reagent R-2

|  | (ml) |
|---|---|
| 0.2M PIPES-NaOH buffer solution (pH 7.3) | 0.05 |
| 0.3% 4-Aminoantipyrine | 0.05 |
| 0.3% TOOS | 0.05 |
| Peroxidase (45 U/ml) | 0.05 |
| Acyl-CoA.oxidase (500 U/ml) | 0.02 |
| 0.2M ATP | 0.01 |
| Water | 0.27 |

The lipases and monoglyceride lipase used for the preparation of the present triglyceride-analyzing reagent may be used in each amount enough to perform the reaction sufficiently. All necessary is to determine the amounts particularly depending on the content of triglyceride to be analyzed. Usually, the monoglyceride lipase may be used in an amount of 0.05 U/ml or more, preferably from 0.1 to 0.5 U/ml, per test, and the lipases in amount of from 50 to 1000 U/ml, preferably from 100 to 500 U/ml. Each of the enzyme may be used as it is, or in the form of a solution in a buffer solution, or in the freeze-dried form.

The glycerol-assaying reagent will be illustrated as follows.

The assaying reagent includes those systems usable in conventional glycerol assay wherein an enzyme acting on the glycerol produced is used. Preferred is an assay which uses a glycerokinase-glycerophosphate oxidase wherein glycero-3-phosphate formed from glycerol in the presence of ATP using glycerokinase is oxidized by the action of glycerophosphate oxidase. Alternatively, an assay using a glycerol oxidase may be used. In these methods, parameters for the assay are hydrogen peroxide which is a final product in these assays, oxygen consumed therein, or dihydroxyacetone phosphate or dihydroxyacetone produced therein. For example, in the glycerokinaseglycerophosphate oxidase method, glycerokinase (0.1–2 U/ml), glycerophosphate oxidase (3–30 U/ml), ATP (1–10 mM), and magnesium ion-generating salt such as magnesium chloride (1–10 mM) which enhances the enzymatic activity of glycerokinase, are added to glycerol produced from triglyceride, whereby hydrogen peroxide and dihydroxyacetone-phosphate are produced through consumption of oxygen. Then, the consumed oxygen may be assayed by means of oxygen electrodes or a dissolved oxygen meter. Alternatively, produced dihydroxyacetone-phosphate is assayed in a conventional manner [Method of Enzymatic Analysis, Vol. 3, 1314–1319]. Assay of the hydrogen peroxide produced may be conducted by an electrochemical method using hydrogen peroxide electrodes. Alternatively, the hydrogen peroxide produced is subjected to a reaction with peroxidase, 4-aminoantipyrine and a coloring reagent such as phenol compounds having the following formula (I) or aniline compounds having the following formula (II), and then the resulting colored material is determined (Japanese Patent Publication No. 3480/1985).

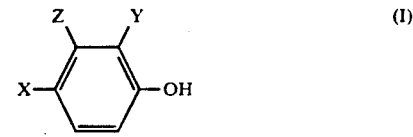
(I)

wherein X is a halogen, Y is hydrogen, a halogen, a lower alkyl or lower alkoxy group, and Z is hydrogen, or a sulfonyl or carboxyl group,

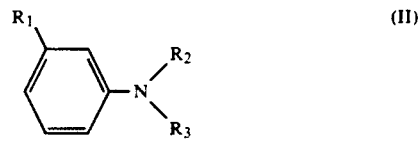
(II)

wherein $R_1$ is hydrogen, or a lower alkyl or lower alkoxy group, and $R_2$ and $R_3$ are each a lower alkyl, lower alkoxy, acetylamide-containing lower alkyl or sulfo-containing lower alkyl group.

Examples of the phenol compounds having the formula (I) are p-chlorophenol, p-bromophenol, 2,4-dichlorophenol, 2,4-dibromophenol and 2,4-dichlorophenolsulfonate. Examples of the aniline compounds having the formula (II) are diethylaniline, N,N-diethyl-m-toluidine, m-methoxy-N,N-dimethylaniline, N-ethyl-N-(3-methylphenyl)-N-acetyl-ethylenediamine, sodium-N-ethyl-N-(3-sulfopropyl)-m-toluidine, and sodium-N-ethyl-N-(2-hydroxy-3-sulfopropyl)-3,5-dimethoxyaniline.

Another assay for hydrogen peroxide is the use of an indicator composition capable of forming a detectable product by a reaction with hydrogen peroxide. The indicator composition may be one capable of being subjected to color change in the presence of hydrogen peroxide. It includes at least one of coloring reagents, fluorescence reagents or luminescence reagents. As the coloring reagents which produce a color change within a visible range, a mixture containing a substance having a peroxidase action and a coloring precursor is used. Peroxidase derived from horseradish is usually used as the substance having a peroxidase action. A combination of 4-aminoantipyrine and the phenol compound having the formula (I) is usually used as the coloring precursor. A combination of 4-aminoantipyrine and the aniline compound having the formula (II) may also be used as the coloring precursor. For example, there is an assay for the hydrogen peroxide wherein an amount of colored materials produced by a reaction among 4-aminoantipyrine, peroxidase and N-ethyl-N-(2-hydroxy-3-sulfopropyl)-m-toluidine (TOOS) may be measured by color intensity. There are assays for measuring an amount of the colored material by color intensity, said material being produced by a reaction between diethylaniline or dimethylaniline and 3-methyl-2-benzothiazolinonehydrazone, or by a reaction between xylenol orange and a tetravalent titanium compound capable of producing a stable red material with hydrogen peroxide. Additionally, there are assays wherein a combination of 2,6-dichlorophenol indophenol and peroxidase, a combination of guaiacum and peroxidase and the like are used as the peroxidase. These indicators may be used in the form of a mixed solution prepared in advance depending on their desired purposes.

In the above reaction using the phenol or aniline compounds, 4-aminoantipyrine and peroxidase, for instance, phenol or TOOS may be used in an amount of about 0.01 to about 0.1%, 4-aminoantipyrine in an amount of 0.01 to 0.05%, preferably 0.03%, and peroxidase in an amount of 3 to 30 U/ml, preferably 4 to 6 U/ml, based on the total reaction mixture, respectively.

In place of the coloring reagent compositions described above, there may be used other reagents, with which the change is spectrophotometrically assayed, for example, fluorescence reagents such as homo-vanillic acid, capable of producing fluorescence by ultraviolet ray irradiation, luminescence reagents, and the like.

In the assay where glycerol oxidase is used, glycerol oxidase (5 to 50 U/ml) is allowed to react to glycerol produced from the triglyceride, whereby dihydroxyacetone and hydrogen peroxide are produced through the consumption of oxygen, and then the consumed oxygen, or the produced dihydroxyacetone or hydrogen peroxide is measured. Preferred is an assay of the hydrogen peroxide produced, which is carried out using the same reagent as that for the assay of hydrogen peroxide in the glycerokinase-glycerophosphate oxidase method. In the case of assay of the consumed oxygen, oxygen electrodes or dissolved oxygen meter may be used as described above. In addition, dihydroxyacetone may be assayed in a known manner [Method of Enzymatic Analysis, Vol. 3, 1442 to 1445].

Furthermore, the quantitative assay of glycerol may be conducted by the following procedures. Glycerophosphate dehydrogenase and NAD are used in place of the above mentioned glycerophosphate oxidase, whereby a reduced NAD is measured by use of known reagents. Another assay is that glycerol produced is subjected to a reaction with ATP and glycerokinase, thereby ADP produced from ATP is measured by use of a reagent used in a known method [Method of Enzymatic Analysis, Vol. 4, 2127 to 2129]. Various reagents familiar to the skilled for glycerol assays may be used to this effect.

In order to facilitate the assay of triglycerides, nonionic surface active agents, additives for enhancing the reaction of producing glycerol and fatty acids from the monoglycerides, and other additives for enhancing activities of enzyme each for assaying the glycerol produced may be used properly. For example, Triton X-100 (a product of Rohm and Haas) as the nonionic surface active agent may be used in an amount of 0.05 to 1%, magnesium chloride as agents for enhancing the glycerokinase in an amount of 1-10 mM and PIPES-NaOH buffer solution as an agent to keep the reaction pH at a fixed value, for example, 6 to 8, preferably at 7.3 at concentration of 20 to 500 mM.

The present reagent for the analysis of triglyceride in accordance with the present invention may be prepared by mixing the lipases and the monoglyceride lipase, together with pre-determined amounts of additives properly selected from th various additives mentioned above, enzymes for assay of the glycerol produced and if desired, the indicators for the hydrogen peroxide produced. The reagent of the present invention may be used in the form suitable for an integrated detection, such as,for example, a kit prepared by coating the reagent on a solid film.

In the analysis of the triglyceride contained in a sample solution, the fatty acids produced at the same time with glycerol may be measured quantitatively, in place of the above-described assay of glycerol which is a component of the monoglyceride. In this case, a reagent for an assay of fatty acid (Japanese Patent Laid-Open No. 8797/1982) may be used in place of the reagent for the assay of glycerol. Any sample solution may be used as long as it contains triglyceride as the substrate for lipases. Examples are body fluids and blood serum. The solution may usually be used in an amount of 0.01 to 5 ml for the analysis. The present invention schematically proceeds as follows, for example, in the case of glycerokinase-glycerophosphate oxidase system:

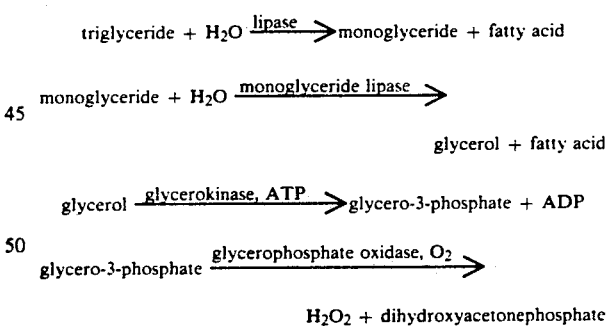

A triglyceride-containing sample solution and a predetermined amount of the reagent for the triglyceride analysis are incubated, and then consumed or produced components according to the above reaction are measured. When the component to be measured is, for example, oxygen, the measurement is carried out using oxygen electrodes or dissolved oxygen meters. No indicator for the hydrogen peroxide is needed. The dihydroxyacetone phosphate produced may also be measured. Among the components to be measured, hydrogen peroxide is preferred. The measurement of hydrogen peroxide is conducted in a colorimetric, fluorometric or luminemetric manner using an indicator for hydrogen peroxide. Alternatively, a hydrogen peroxide electrode meter such as an oxidase meter manufactured by YSI company may be used.

The reaction between the present reagent and the sample solution containing triglyceride is carried out for a predetermined period of time at a predetermined temperature, preferably 25° to 40° C., and then some components consumed or produced thereby are measured.

After the oxygen consumed or the hydrogen peroxide produced is quantitatively measured by any of the methods as described above, quantitative calculation of triglyceride is made using the corresponding calibration curve. In the quantitative measurement of hydrogen peroxide using the indicator, the absorbance is measured at a wave length suitable for the colorimetry using the indicator, such as, for example, at 600 nm, or that suitable for the fluorometry.

According to the present invention, the reagent for the triglyceride analysis comprising lipases and the monoglyceride lipase is provided, and various analytical methods may be carried out effectively using the same. For example, in the field of clinical diagnostics, wherein the triglyceride analysis is carried out using automatic analyzing instruments, it is possible to carry out the analysis with excellent accuracy within a short period of time even for a sample containing triglyceride at a high concentration.

The present invention will be explained in more detail with reference to the following Examples, which are only illustrative, but not limitative.

EXAMPLE 1

Composition of a reagent for analyzing triglycerides contained in blood serum

| | |
|---|---|
| PIPES-NaOH pH 7.3 (other various good buffers) | 100 mM |
| ATP | 5 mM |
| MgCl$_2$ | 2 mM |
| Glycerokinase | 0.7 U/ml |
| Glycerophosphate oxidase | 5.0 U/ml |
| Peroxidase | 5.0 U/ml |
| Nonionic surface active agent (Triton X-100) | 0.2% |
| Lipase | 233 U/ml |
| Monoglyceride lipase | 0.15 U/ml |
| 4-Aminoantipyrine | 0.03% |
| DAOS * | 0.03% |

DAOS * 3,5-Dimethoxy-N-ethyl-N-(2-hydroxy-3-sulfopropyl)-aniline

Each 20 μl of blood serum as a sample solution was added to 3.0 ml of respective triglycerides analysis reagents having the above composition (lipase content: 300 U/ml) with or without monoglyceride lipase (0.2 U/ml), and each mixture was allowed to react at 37° C. According to the lapse of time, the absorbance was measured at 600 nm.

Figure 1:
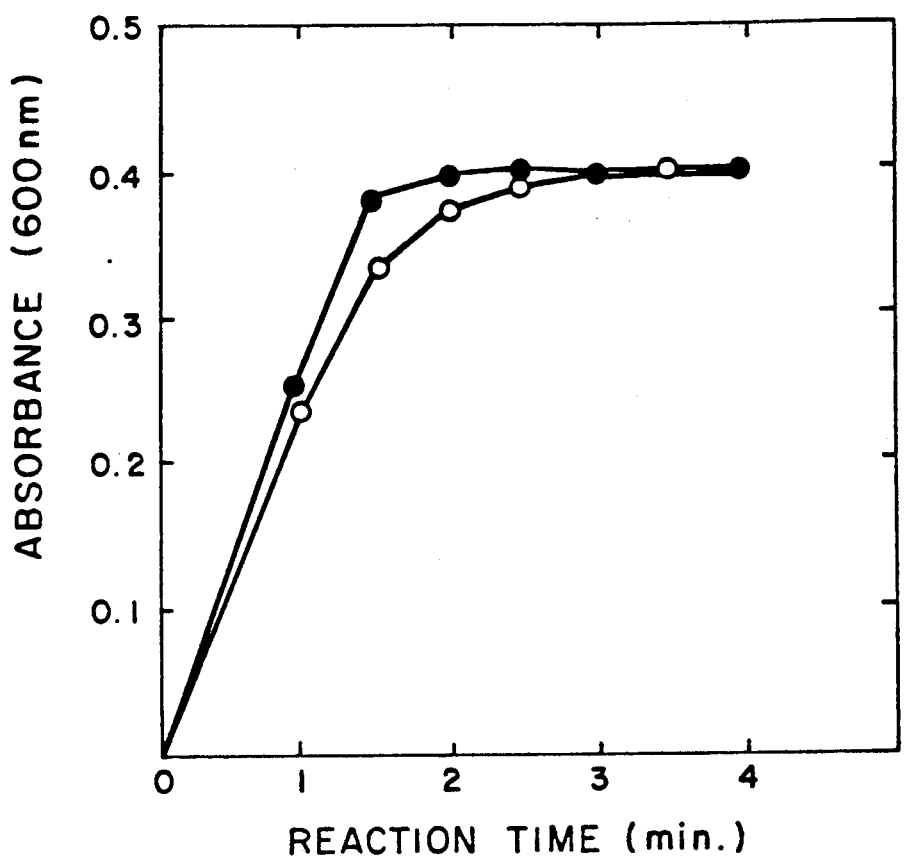
FIG. 1 shows a period of time required for the reaction in the absence or presence of the monoglyceride lipase in an amount of 0.2 U/ml.

As shown in FIG. 1, in case of the addition of no monoglyceride lipase (O), the termination of the reaction was unclear, but seemingly after about 3.5 minutes, while, in case of addition of 0.2 U/ml of monoglyceride lipase (●), the reaction reached equilibrium and terminated in 2 minutes.

EXAMPLE 2

Each 20 μl of blood serum as a sample solution was added to 3.0 ml of respective triglyceride analysis reagents having the above composition (lipase content being U/ml), and containing monoglyceride lipase in each varied amount from 0 to 0.2 U/ml, and each mixture was allowed to react at 37° C. The time required for the completion of color reaction was measured.

Figure 8:
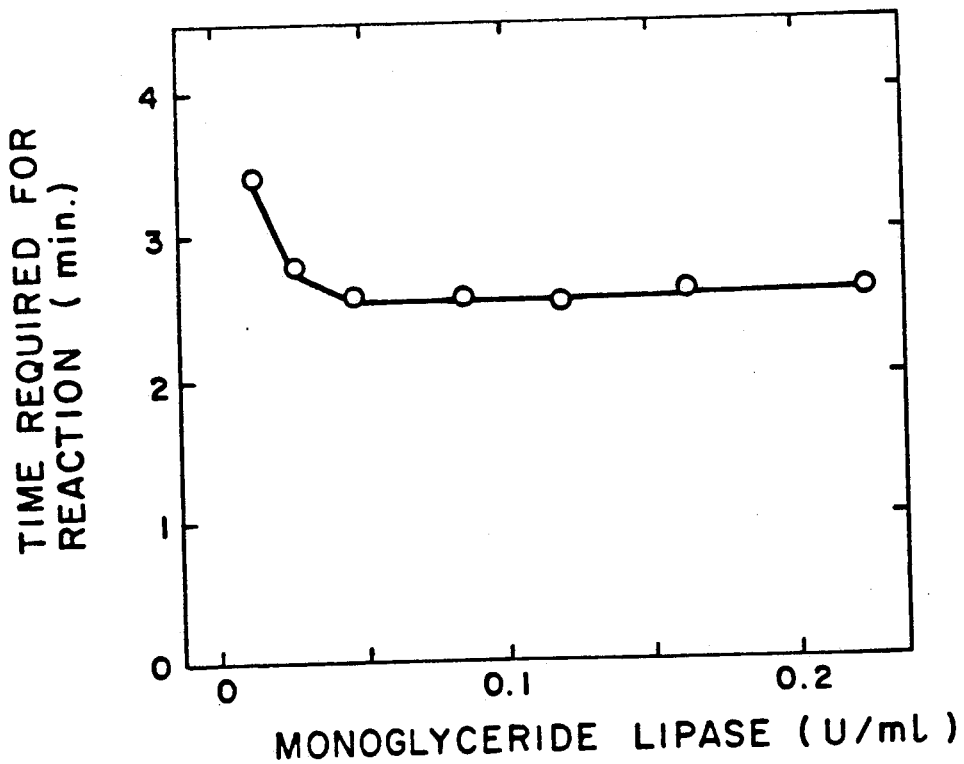
FIG. 8 shows an effect of shortening a reaction time in the analysis of triglyceride in sera in the presence of the monoglyceride lipase.

As shown in FIG. 8 (-O-), the shortening effect of the reaction time becomes unchanged as monoglyceride lipase added is in an amount of 0.05 U/ml or more, preferably 0.1 U/ml.

EXAMPLE 3

Each 20 μl of a diluted solution of a high neutral fat serum was added to respective triglyceride analysis reagents having the above composition (lipase content: 300 U/ml) and containing no monoglyceride lipase (-O- shown in FIG. 9) or 0.2 U/ml of monoglyceride lipase (-●- shown in FIG. 9), and each mixture was allowed to react at 37° C. for 3 minutes. The absorbance was measured at 600 nm.

Figure 9:
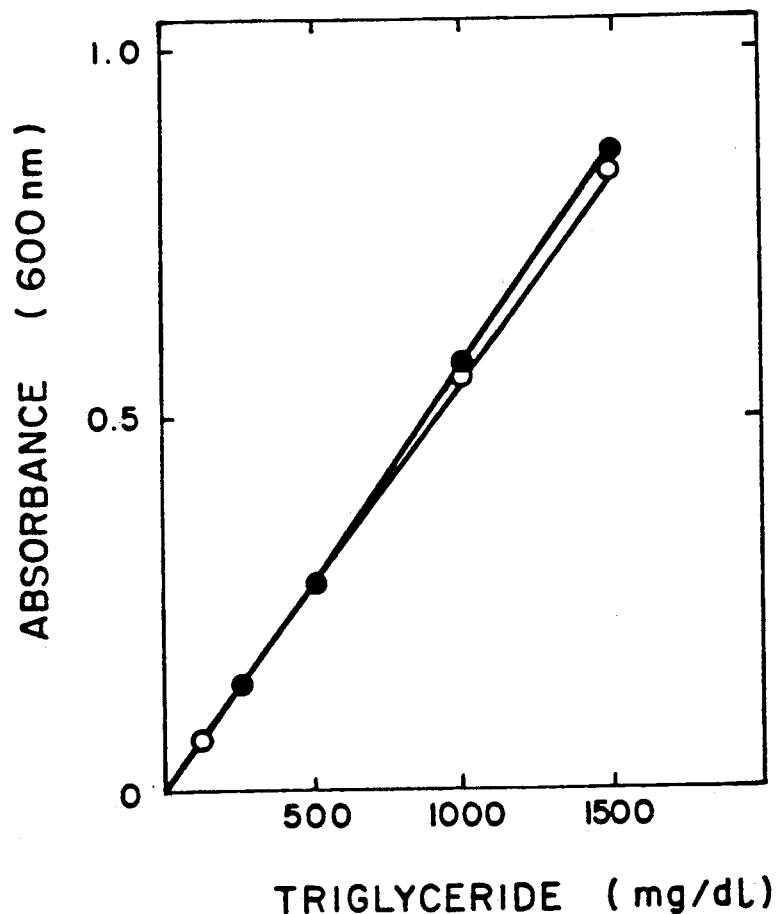
FIG. 9 shows a difference between calibration curves of triglyceride in the absence and in the presence of the monoglyceride lipase in an amount of 0.2 U/ml.

As shown in FIG. 9, the results reveal that the triglyceride is measured linearly upto 1500 mg/dl in case of using the reagent containing 0.2 U/ml of monoglyceride lipase.

We claim:

1. A reagent for analysis of triglycerides, which comprises triglyceride lipases and a monoglyceride lipase wherein the monoglyceride lipase is obtained from *Bacillus stearothermophilus* H165 strain (FERM BP-1673) and is capable of acting on monoglycerides but not on di- or tri-glycerides.

2. A reagent for the analysis of triglycerides according to claim 1 which further comprises glycerokinase, glycerophosphate oxidase and adenosine triphosphate.

3. The reagent for the analysis of triglyceride according to claim 2, wherein the reagent for assaying glycerol contains at least one indicator which can react with H$_2$O$_2$ to change an optical characteristic.

4. The reagent for the analysis of triglyceride according to claim 3, wherein the indicators are color reagents, fluorescence reagents or luminescence reagents.

5. The reagent for the analysis of triglyceride according to claim 4, wherein the coloring reagents contain 4-aminoantipyrine, N-ethyl-N-(2-hydroxy-3-sulfopropyl)-m-toluidine, phenol and peroxidase.

6. A method for analysis of triglyceride by bringing lipase into contact with a sample solution containing triglyceride, and measuring the liberated glycerol or fatty acid, comprising providing a monoglyceride lipase which is obtained from *Bacillus stearothermophilus* H-165 strain and is capable of acting on monoglycerides but not on di- or triglycerides, contacting a system containing triglyceride lipase and the monoglyceride lipase with the sample solution, and then measuring a component consumed or produced in a reaction for measuring the glycerol or fatty acids.

7. The method for analysis of triglyceride according to claim 6, wherein the system containing the monoglyceride lipase and a triglyceride lipase additionally comprises glycerokinase, glycerophosphate oxidase and adenosine triphosphate.

8. A reagent for the analysis of triglycerides according to claim 1 which further comprises glycerokinase and glycerophosphate dehydrogenase.

9. A reagent for the analysis of triglycerides according to claim 1 which further comprises glycerol oxidase.

10. A reagent for the analysis of triglycerides according to claim 1 which further comprises glycerokinase.

11. The method for analysis of triglyceride according to calim 6, wherein the system containing triglyceride lipase and the monoglyceride lipase additionally comprises glycerokinase and glycerophosphate dehydrogenase.

12. The method for analysis of triglyceride according to claim 6, wherein the system containing triglyceride lipase and the monoglyceride lipase additionally comprises glycerol oxidase.

13. The method for analysis of triglyceride according to claim 6, wherein the system containing triglyceride lipase and the monoglyceride lipase additionally comprises glycerokinase.

* * * * *